United States Patent [19]
Montlick

[11] Patent Number: 5,561,446
[45] Date of Patent: Oct. 1, 1996

[54] METHOD AND APPARATUS FOR WIRELESS REMOTE INFORMATION RETRIEVAL AND PEN-BASED DATA ENTRY

[76] Inventor: Terry F. Montlick, 71 Judson La., Bethlehem, Conn. 06751

[21] Appl. No.: 385,078

[22] Filed: Feb. 7, 1995

Related U.S. Application Data

[63] Continuation of Ser. No. 189,137, Jan. 28, 1994, abandoned.
[51] Int. Cl.$^6$ .................................................. G09G 5/00
[52] U.S. Cl. ........................... 345/173; 455/66; 455/54.1; 364/413.02
[58] Field of Search ..................................... 345/158, 173, 345/179, 146, 902, 115, 123; 364/413.02; 340/825, 825.36; 178/18, 19; 455/66, 33.4, 54.1

[56] References Cited

U.S. PATENT DOCUMENTS

| | | | |
|---|---|---|---|
| 4,677,585 | 6/1987 | Ikegami et al. | 345/123 |
| 4,698,624 | 10/1987 | Barker . | |
| 5,063,600 | 11/1991 | Norwood | 345/145 |
| 5,086,392 | 2/1992 | Nakajima | 345/115 |
| 5,194,852 | 3/1993 | More | 345/173 |
| 5,241,303 | 8/1993 | Register | 345/168 |
| 5,241,542 | 8/1993 | Natarajan | 455/54.1 |
| 5,276,794 | 1/1994 | Lamb | 345/173 |
| 5,313,051 | 5/1994 | Brigida | 345/173 |

OTHER PUBLICATIONS

Docs, Inc. brochure for SOAPware.
PI Systems Visiting Nurse Health System uses electronic pen clipboards . . . brochure.
News Release from Healthcare Communications for "Hippocrates".
Telxon Corporation News release dated Feb. 14, 1994 for point and chose pen based computing.
Case study "Pace for Hospitals? Ask Karen Bossard" by PACE, Health Care Expert Systems, Inc.
New release by Proxim, Inc. "Proxim & Penknowledge Team Up for Pen-Based Networking in Medical Industry".
The brochure "Tired of Heavy Metal? Grab a ScratchPad" by Greycat, Inc.
Medical Pen Systems brochure.
"Health Care Information Technology with Reform Imminent Health Care Looks to . . . " Sep./Oct. 1993, pp. 24, 26, 27, 45 & 46.
Systems Plus, Inc. brochure for Med-Pad System.
PI Systems Corporation brochure for Infolio 160.

*Primary Examiner*—Richard Hjerpe
*Assistant Examiner*—Kent Chang
*Attorney, Agent, or Firm*—David P. Gordon

[57] ABSTRACT

A method and system for wireless remote information retrieval and pen-based data entry includes a central computer system having a relatively large storage capacity and/or access to relatively large storage devices and coupled to a wireless network having a plurality of cells. One or more portable pen-based computers are provided with wireless communication capability for connecting with the central computer system through the wireless network. The central computer system is provided with software for accessing a plurality of digitally stored forms and transmitting those forms to the pen-based computers in response to selection requests from the pen-based computers. A selected form is displayed on the screen of the pen-based computer which requested it and data is entered through the pen-based computer by handwriting on the display of the form. The central computer system receives the hand written data as electronic ink and associates the electronic ink file with the form upon which it was written. The form and its associated electronic ink file are stored in the central computer system or in a storage device to which the central computer system has access. The hand written data entered through the pen-based computer is thus associated with other data which can be recalled and/or associated with yet other data without recognizing the handwritten data as text.

20 Claims, 12 Drawing Sheets

```
                          ┌─ 33
┌─────────────────────────────────────────┐
│  PHYSICAL-JOHN Q PUBLIC,ID#123456789 9/2/93 │
├─────────────────────────────────────────┤
```

FIG. 3

Form fields shown:

- VITAL SIGNS: HGT:, WT:, BP: RA= / LA= /, P=, RR=, T=
- HEENT 30
- EYES:
  - ICTERUS: ☐- ☐+     OCULAR DYSMOTILITY: ☐- ☐+
  - ARCUS: ☐- ☐+      PUPILLARY DYSMOTILITY: ☐- ☐+
  - XANTHALASMA: ☐- ☐+   PAPILLEDEMA: ☐- ☐+
  - PTOSIS: ☐- ☐+      PROPTOSIS: ☐- ☐+
  - RETINOPATHY: ☐- ☐+
- EARS:
  - EARS: ☐- ☐+
  - HEARING: ☐- ☐+
- OTHER:
  - PHARYNGITIS: ☐- ☐+
  - ADENOPATHY: ☐- ☐+
  - (MORE)

Side tabs (32): PDR | HISTORY | PHYSICAL | DIAGNOSIS | PROCEDURES | LABORATORY | PERSCRIPTIONS | PREFERENCES Bottom toolbar (34): ? HELP | $ BILLING | 🗐 PATIENT | ⇦ PREVIOUS | ⇨ NEXT Labels: 50, 12a

PHYSICAL-JOHN Q PUBLIC,ID#123456789 9/2/93 — 33

VITAL SIGNS
HGT: 67.5 —51
WT: 168 —51          *large cuff*
BP:    RA= 120/94    LA= 110/90       52
P= 88 —51   RR= 30 —51   T= 98.8
                              51            30

HEENT

*deep optic cupping*
ICTERUS: ☑-☐+    OCULAR DYSMOTILITY: ☑-☐+     52  EYES
ARCUS: ☑-☐+   PUPILLARY DYSMOTILITY: ☑-☐+   *asteroid hyalosis*
XANTHALASMA: ☑-☐+    PAPILLEDEMA: ☑-☐+
PTOSIS: ☑-☐+         PROPTOSIS: ☑-☐+
RETINOPATHY: ☑-☐+ 51       51

EARS: ☐-☑+ TM                               EARS
         AS   *retracted TM*
   51              53
HEARING ☑-☐+

PHARYNGITIS: ☐-☑+  *petechial*              OTHER
       51
ADENOPATHY: ☐-☑+  AXILLARY BILAT   REACTIVE/TENDER
                  SCALENE H        RUBBERY
                           51

(MORE)

?      $       📄              ⇦          ⇨
HELP  BILLING  PATIENT         PREVIOUS   NEXT

Tabs: HISTORY | PDR | PHYSICAL | DIAGNOSIS | PROCEDURES | LABORATORY | PERSCRIPTIONS | PREFERENCES

FIG. 3a

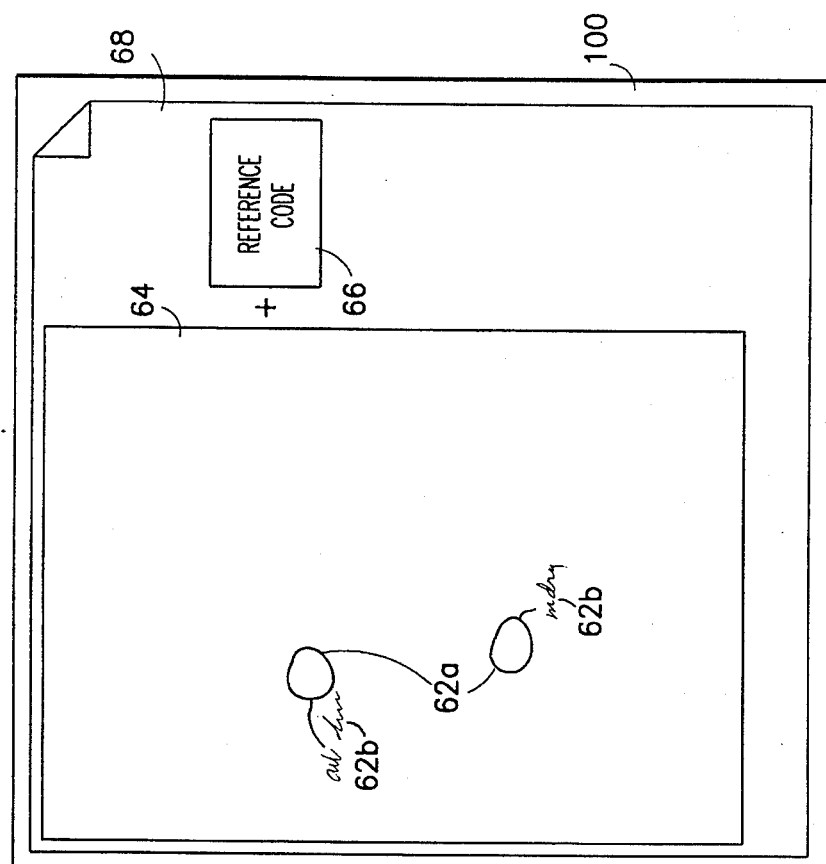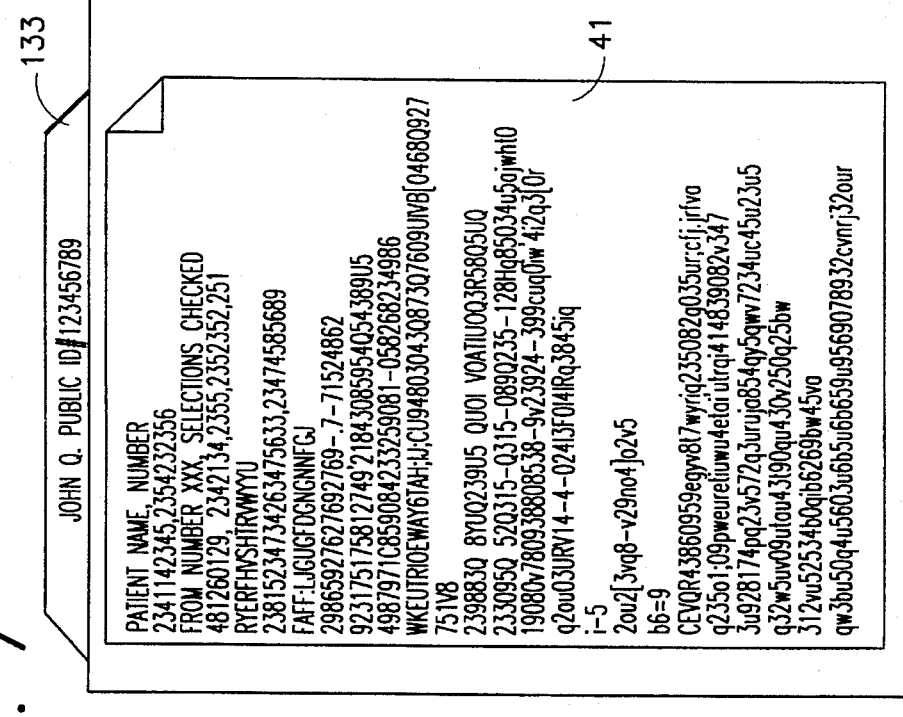
FIG. 7A
FIG. 7
| FIG. 7A |
| FIG. 7B |

METHOD AND APPARATUS FOR WIRELESS REMOTE INFORMATION RETRIEVAL AND PEN-BASED DATA ENTRY

This application is a continuation of application Ser. No. 08/189,137 filed on Jan. 28, 1994, now abandoned.

BACKGROUND OF THE INVENTION

1. Field of the Invention

The invention relates to wireless remote pen-based data terminals and to methods for their use. More particularly, the invention relates to a portable pen-based computer which is coupled by a wireless network to a host computer which supplies the portable computer with data and with forms such that data and drawings can be entered by a stylus on the forms and stored in the host computer. The invention is particularly well suited for medical applications such as entering and retrieving patient information.

2. State of the Art

Remote data entry and retrieval is ubiquitous in all phases of modern life from business and industry to education and entertainment. In its basic form, a remote computer or terminal is coupled to a host computer through a digital network or modem connection. The host computer generally provides the terminal with menus and/or a graphical interface through which information may be exchanged. Information is entered or retrieved by a remote terminal using a keyboard and/or a mouse.

Despite the widespread use of computer terminals for the entry and retrieval of information, paper forms and pens are still necessary for the collection of information in many situations. The primary reasons why information is still collected in this way include portability, ease of use, and independence from electrical power requirements. For example, in the medical profession, which is otherwise technologically quite sophisticated, information on patients is routinely collected by nurses and physicians using pre-printed paper forms and pens. This information is then later transcribed by clerks using computer terminals so that the information can be stored for later retrieval.

Portable computers and modern operating systems have alleviated the need for paper data entry in some areas. Recent developments in nickel metal hydride (NiMH) battery technology have expanded the useful life of portable computers to eight hours or more between charges. In addition, graphical user interfaces have eliminated the need to learn arcane commands in order to use a computer. Yet, while it is ultimately more efficient to enter data directly into a computer, it is still often much easier to collect data using a pen and paper. This is particularly true when the person collecting the data is travelling from one location to another, such as a doctor visiting patients in an office or hospital. A portable computer must be placed on a flat surface or the user's lap and generally requires the use of both hands and a minimum typing skill. The computer is therefore not nearly as convenient as holding a clipboard or note pad in one hand and a pen in the other whereby notes may be made quickly and easily.

Recently, small portable pen-based computers have been introduced. Pen-based computers are capable of connecting with a host computer through a wireless network. Pen-based computers typically do not have a keyboard or a mouse. They provide a position sensitive LCD display and a stylus for touching locations or writing or drawing on the display. Menu items displayed on the position sensitive display can be selected by pressing the display with the stylus at the location on the display where the menu item appears. Some pen-based computers such as the APPLE NEWTON MESSAGE PAD and the AT&T EO attempt handwriting recognition, although the accuracy of handwriting recognition technology is quite variable. Typically, the user must develop a clear and consistent handwriting style in order for the pen-based computer to recognize the handwriting as coded text. It typically takes from several hours to several weeks to train the computer to recognize the handwriting of a particular user, after which time the computer is "personalized" to that particular user. Most users are unwilling or unable to provide sufficiently clear and consistent handwriting or to take the time necessary to train the computer or tho have the computer train the user to write neatly and consistently. Some pen-based computers may optionally not attempt to recognize handwriting, but instead store the handwriting as "electronic ink". Electronic ink can presently be saved, for example, in a standardized file format called JOT which is a type of graphic file format that does not interpret the meaning of the handwriting but only saves the sequence of stylus strokes of the handwriting. The advantages of saving handwriting as electronic ink are that there is no loss in accuracy by attempting to convert it to typed text and the user does not need to train the computer. One of the disadvantages of saving handwriting as electronic ink, however, is that electronic ink remains unintelligible to a computer and the information contained in the handwriting cannot be related to other information by the computer. Electronic ink, though, may be processed at any later time by more powerful handwriting recognition algorithms than may be resident on a pen computer, or which have yet to be developed.

SUMMARY OF THE INVENTION

It is therefore an object of the invention to provide a method and system for relating handwriting to other information without attempting to convert the handwriting to typed text.

It is also an object of the invention to provide a method and system for collecting and organizing handwritten information in real time from a pen-based computer using a wireless network.

It is another object of the invention to provide a method and system for providing remote access to an information data base through a pen-based computer using a wireless network.

It is still another object of the invention to provide an interface for a pen-based computer whereby handwritten information can be ascribed meaning without recognizing handwritten characters as text.

In accord with these objects which will be discussed in detail below, the method and system of the present invention includes a central computer system, such as a single computer in a network of computers, which is coupled to a wireless network having a plurality of cells, and has a relatively large storage capacity and/or access to relatively large storage devices. One or more hand held pen-based computers are provided with wireless communication capability for connecting with the central computer system through the wireless network. The central computer system is provided with software for accessing a plurality of digitally stored forms and transmitting those forms to the pen-based computers in response to selection requests from the pen-based computers. A selected form is displayed on the screen of the pen-based computer which requests it and data is entered through the pen-based computer by handwriting on the position sensitive display which displays the form. The central computer system receives the data as electronic ink and associates the electronic ink file with the form which was displayed when the electronic ink file was created. The form and its associated electronic ink file are stored in the central computer system or in a storage device to which the central computer system has access. The handwritten data entered through the pen-based computer is thus associated with other data which can be recalled and/or associated with yet other data without the need to recognize the handwritten data as text.

According to a presently preferred embodiment of the invention, the central computer system is DOS based or has a DOS based computer acting as a gateway. The central computer system is coupled to a spread-spectrum wireless local area network available from Proxim, Inc. which allows continuous data communication at a rate of approximately 1.6 Mbps. The pen-based computers are preferably ULTRALITE VERSAs from NEC and are each provided with a PCMCIA card from Proxim, Inc. which gives them access to a wireless local area network. The pen-based computers are programmed with network communication software, such as Netware from Novell, which interacts in real time through the wireless network with the central computer system. In the preferred embodiment, the pen-based computers run software created with the PENRIGHT development system available from AST Research. This provides the pen-based computers with the ability to interact with the user in the ways described herein.

The user of the pen-based computer chooses a form by selecting it from a menu with the stylus whereupon the form is displayed on the position sensitive display of the pen-based computer. The forms typically consist of lists of items each having a check box which may be checked with the stylus and/or spaces in which information may be written and/or drawings provided using the stylus as a writing instrument. In the case of check boxes, the data entered by touching the stylus to the check box can be immediately related by the central computer system to the information corresponding to the check box. In the case of spaces in which information and/or drawings are handwritten or drawn, the handwritten information or drawing is stored as electronic ink and associated with the form on which the handwritten information is written. No attempt is made to recognize the handwriting as coded text. Some forms may include a "virtual keyboard" for entering text to be recognized as text. The virtual keyboard is displayed as a picture of a QWERTY keyboard and characters are entered by touching the stylus to the characters displayed.

By associating electronic ink files with digitally stored forms, the data entered through the pen-based computers is given meaning and the ability to be recalled and associated with other information by the central computer system. Additionally, since no handwriting recognition is attempted, the pen-based computers are fungible and may be used by anyone without the need to train and personalize the pen-based computers.

The primary application contemplated by the invention is in the field of health care where a wireless network is deployed throughout an office or hospital, for example, and physicians and nurses have access to patient records and other information through the wireless pen-based computers. In this application, the central computer system supplies the pen-based computers with a selection of standard medical forms such as patient history or physical forms. Physicians and nurses can access forms for a particular patient by selecting the name of the patient from a menu provided to the pen-based computers by the central computer system. The forms for the selected patient will be displayed on the pen-based computer and information may be entered on the form with the stylus. Similarly, forms which already contain information on the selected patient may be recalled and viewed by the physician or nurse using the pen-based computer. The pen-based computer therefore provides both read and write access to patient forms and forms may be write protected and/or read protected using passwords and/or other known techniques. In addition to accessing patient record forms, the central computer system may be coupled to other information storage devices such as CD-ROMs and provide the pen-based computers with a large library of information such as the Physician's Desk Reference, the Merck Manual, and the like. Moreover, the networking capability of the central computer system and the pen-based computers may also provide various types of messaging abilities to the pen-based computers for ordering prescriptions and laboratory tests, billing, scheduling, etc.

Additional objects and advantages of the invention will become apparent to those skilled in the art upon reference to the detailed description taken in conjunction with the provided figures.

BRIEF DESCRIPTION OF THE DRAWINGS

FIG. 3 is a view of a typical screen display provided on a pen-based computer for receiving input in the form of electronic ink;

FIG. 3a is a view similar to FIG. 3 showing information in the form of electronic ink on the screen display;

FIGS. 8 and 8a are views similar to FIG. 5 showing how portions of an illustration are identified by stylus input.

DETAILED DESCRIPTION OF THE PREFERRED EMBODIMENTS

Figure 1:
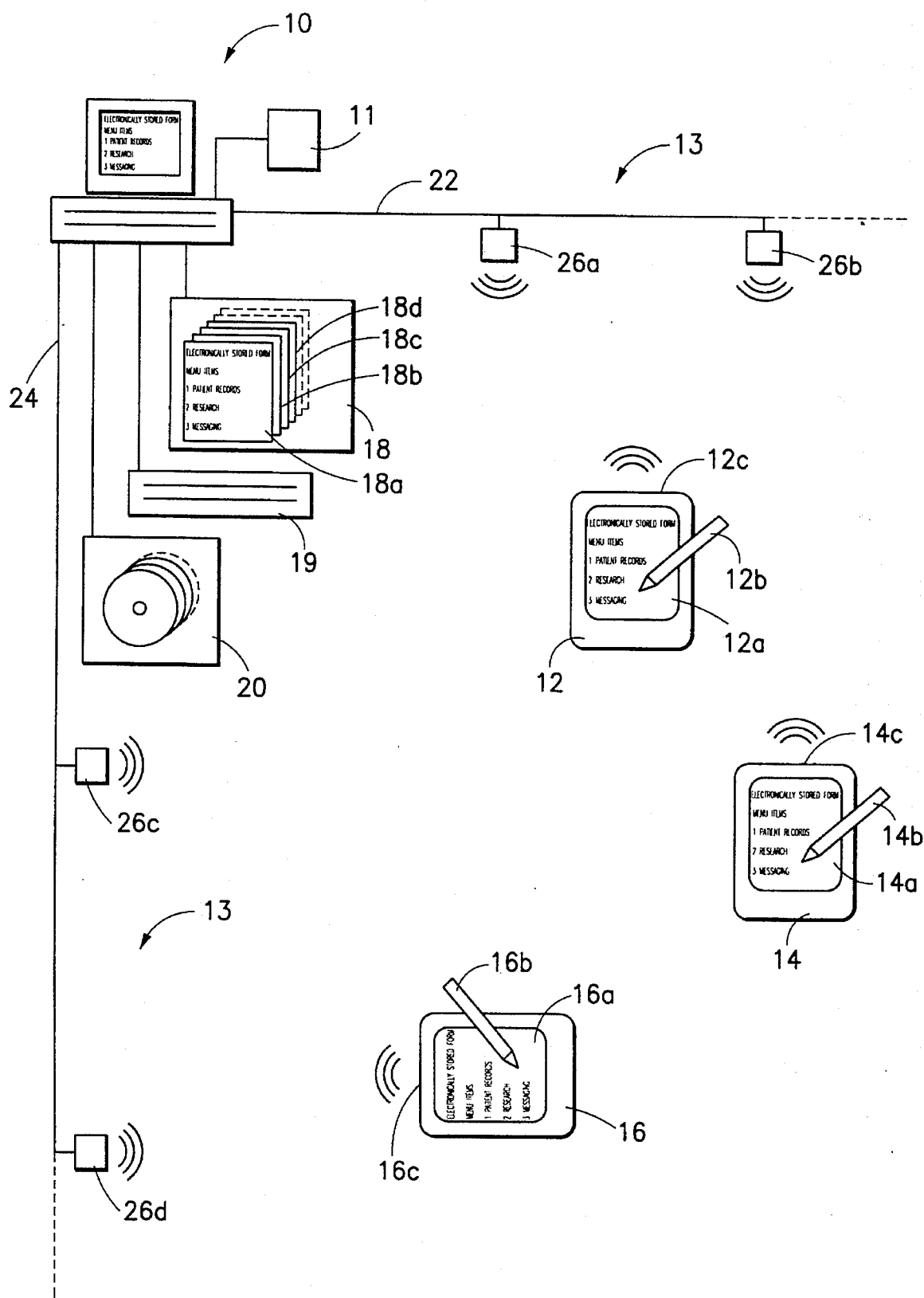
FIG. 1 is a schematic diagram of one implementation of the method and system of the invention.

Referring now to FIG. 1, the system of the invention is preferably implemented in a system which includes a central computer system 10 and a plurality of portable pen-based computers 12, 14, 16. The central computer system 10 is preferably a DOS-based INTEL processor having access to memory 18 containing a plurality of digitally stored medical forms 18a, 18b, 18c, 18d, ... etc. These forms may be stored as formatted text or as image files or in any other manner consistent with industry standards. The same memory 18 or disk storage 19 is made accessible to the central computer system 10 for storage of patient records and or other information as described more fully below. Preferably, the central computer system 10 also has access to a library of medical information such as the Physician's Desk Reference and the Merck Manual which may be in the form of CD-ROM disks 20. The central computer system 10 may also be advantageously coupled to a modem 11 for communicating with other networks and/or for the transmission and reception of FAX information.

A spread-spectrum wireless network 13 including a plurality of radio transceivers 26a, 26b, 26c, 26d, . . . etc. is coupled to the central computer system 10 by network cables 22, 24, etc. Each transceiver defines a radio communication cell having a radius of approximately 300–500 feet. Therefore, the number location of transceivers which are coupled to the network will depend on the topography of the site served by the invention. For example, in a hospital, transceivers might be located in corridors and spaced apart several hundred feet so that cells overlap and the entire area is covered by cells. A suitable wireless network is available from Proxim, Inc., Mountain View, Calif.

Each portable pen-based computer 12, 14, 16, . . . , etc. is provided with a position sensitive display 12a, 14a, 16a, . . . , etc., a stylus 12b, 14b, 16b, . . . , etc., and a wireless network transceiver 12c, 14c, 16c, . . . , etc. A suitable pen-based computer is the ULTRALITE® VERSA™ which is available from NEC Technologies, Inc., Boxborough, Mass. The wireless network transceiver is preferably provided in the form of a PCMCIA card available from Proxim, Inc. which is easily installed in the ULTRALITE® VERSA™. The PROXIM system provides for a continuous spread-spectrum bi-directional radio link between the portable pen-based computers 12, 14, 16, . . . , etc. and the central computer system 10 which allows for data communication at a rate of 1.6 Mbps and uninterrupted "roaming" between overlapping cells.

According to the invention, each portable pen-based computer 12, 14, 16, . . . , etc., is provided with a graphical interface 30 through which digitally stored forms and other information may be retrieved from the central computer system 10 via the wireless network 13 and through which data may be entered using the stylus. Software for providing the graphical interface is preferably developed in the PEN-RIGHT development environment which is available from AST Research. Those skilled in the art will appreciate that the graphical interface is preferably provided as part of each pen-based computer but may be provided to the pen-based computers by the central computer system.

Figure 2:
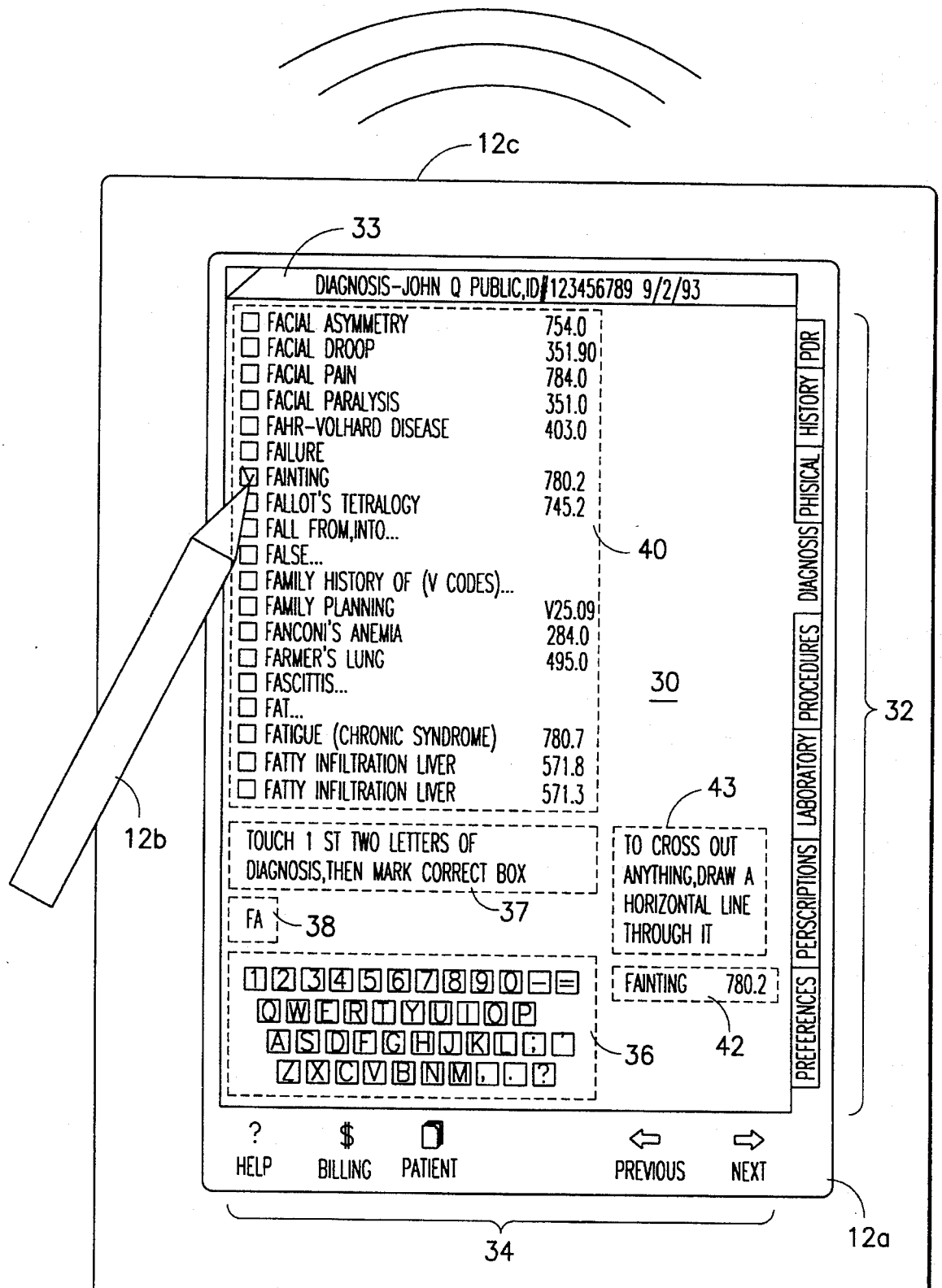
FIG. 2 is view of a typical screen display provided on a pen-based computer for receiving menu selection input from a stylus.

As shown in FIG. 2, a graphical interface 30 is displayed on the position sensitive display 12a of the portable pen-based computer 12. The interface 30 determines what will be displayed on the position sensitive display 12a and how portions of the position sensitive display 12a will respond to touching by the stylus 12b. For example, according to a preferred embodiment of the invention, the interface 30 displays a menu field 32 for selecting information and/or forms from sub-fields (menu items) such as PDR (Physician's Desk Reference), Physical, Diagnosis (ICD-9 system), Procedures (CPT procedure codes), Services (physical therapy, respiratory therapy, etc.), and for ordering tests from the Laboratory and Prescriptions from the pharmacy. Each of the sub-fields of menu field 32 defines a portion of the display 12a which is stylus responsive in a particular way. For example, touching the stylus 12b to one of these sub-fields in the menu field 32 causes the interface 30 to display different information or forms on the display 12a as described more fully below. The type of information or form being displayed is indicated in the headline field 33 at the top of the display 12a. In addition to the menu field 32 and the headline field 33, the interface 30 may include a standard functions field 34 having sub-fields (icons) for performing certain computer functions such as Previous screen, Next screen, Help screen, for entering notes in a Notebook, or for switching between Patient records and Billing records.

The graphic interface 30 is comprised of two parts. The first part is the means by which software running on a pen computer receives information about stylus position and status. This is typically provided by the pen computer hardware, and processed into a convenient form by the pen computer's operating system software for use by the second part of the graphic interface. The second part of the graphic interface consists of the computer program which generates and operates the form windows, menus of choice lists, and virtual controls, such as a virtual keyboard. This portion of the interface means receives events generated via the stylus, and performs the appropriate actions described herein. It communicates with the graphic user interface system software of the first part of the graphic interface.

The first part of the graphic interface 30 includes the pen computer's built-in hardware digitizer, which determines the x and y screen pixel coordinates of the stylus at periodic intervals, along with its up/down status, that is the determination of whether or not the stylus is touching the surface of the screen. These stylus coordinates are read by system software, which organizes them into event data which are passed to the second part of the graphic interface. This event data include not only the stylus coordinates and up/down status, but if the stylus was in a screen window, control area, field, or other significant sub-area of the screen. Other, higher level events are generated which operate windows and on-screen virtual controls that have been set up by the second part of the interface means. Events are generated if a window is entered for the first time by the stylus, if a window is exited, if a control is entered, if a field is entered, etc. In the preferred embodiment, the PenRight system software is used to provide events to the second part of the graphic interface, as well as the capability to generate form windows, menus, and virtual controls. Such a means for input from a positioning device such as a stylus and outputting organized information to a computer screen constitute the system software for what is commonly known as a "graphic user interface".

In the preferred embodiment, the second part of the interface means is written in the C++ language. This computer language is particularly well suited for this invention because it can efficiently run on a portable pen computer, and it is also object-oriented, a capability which is particular powerful when used in the event-driven environment of a pen computer. C++ is a superset of the C language, is being standardized by the American National Standards Institute (ANSI), and is widely available on nearly all computer systems. In the preferred embodiment, the Borland (Scotts Valley, Calif.) C++ compiler is used to compile C++ source code, though the Microsoft (Redmond, Wash.) C++ compiler, or any other C++ compiler could be used as well.

The events which are delivered to the second part of the interface means by the first part of the interface means are sent as messages (function calls) to C++ objects. These objects are instances of C++ classes, and directly correspond to forms on the pen computer screen. The behavior and functionality of a screen form is entirely determined by its C++ class. Because C++ has the object-oriented property of "inheritance", sophisticated C++ form classes can be built out of simpler ones, and inherit all of their functionality. The event messages are passed up the inheritance hierarchy by C++ so they can be automatically handled by the appropriate C++ class.

For example, a C++ class called a "thermometer" can display an illustration of a thermometer on the screen, which the user can then interact with by sliding the line of "mercury" using the stylus. The thermometer class makes use of a "barCtl" class, which displays the temperature of the thermometer as a horizontal bar, and allows the stylus to change it. Rather than having to be written from scratch, the C++ thermometer class can not only utilize a barCtl class, but be derived from a "numberForm" class, which understands how to display and process numbers. The numberForm class is derived from a "fieldForm" class, which has the functionality to process a generic field, be it a number, character string, or any other type of information. Finally, the fieldForm class is derived from a "form" class, which has the basic capabilities to display a form on the screen, remove it from the screen, and changing from one form to another. Anyone skilled in the art can appreciate the ease with which the second part of the interface means of this invention may be implemented, modified, and extended using the C++ language.

As shown by example in FIG. 2, the Diagnosis menu item has been chosen and the graphic interface 30 has caused the display 12a to display fields appropriate to this selection. For example, field 36 displays a virtual keyboard which is responsive to touch from the stylus 12b. Instructions for using the virtual keyboard are displayed in field 37 which is typically not responsive to touch from the stylus 12b. Letters touched on the virtual keyboard are displayed in field 38. The letters typed, in this case FA, results in an alphabetical listing of diagnoses beginning with the letters FA being displayed in field 40. All of the names listed in field 40 include a check box to the left. Touching the check box with the stylus 12b chooses the diagnosis and the chosen diagnoses are displayed in field 42. Instructions for deleting a diagnosis are displayed in field 43. Some of the diagnoses listed in field 40 (such as "Facial Asymmetry") indicate their respective ICD-9 number (such as "754.0") to the right of the diagnosis name. Other diagnosis names (such as "Failure . . .") are followed by ellipses and no number. These latter names refer to a class of diagnoses which can be displayed in a sub-listing by touching the box to the left of the name with the stylus 12b.

Those skilled in the art will appreciate that the headline field 33, as shown in FIG. 2, displays the name and ID# of a patient as well as the date. Clearly, the diagnosis data entered on this form is meaningless without relating the information to a particular patient. According to the interface 30 shown in FIG. 2, a patient may be selected by touching the Patient icon in the functions field 34 with the stylus 12b, after which an alphabetical patient listing will be displayed in field 40 and a virtual keyboard will be displayed in field 36. By touching the first two letters of the patient's surname on the virtual keyboard with the stylus 12b, field 40 will list patients whose surname begins with those letters. Touching the Previous or Next icon in the functions field 34 with the stylus 12b will scroll the listing in field 40. It will be appreciated that this type of "multiple choice" data entry discussed thus far is digital by nature, is readily recognizable by the central computer system, and is easily stored and associated with a particular patient's records. In addition to this type of multiple choice data entry, however, the invention provides for handwritten input of unique information which is not selected from a menu listing. The information is transmitted automatically to the central computer system via the wireless network. In the preferred embodiment, this happens when the file or files which locally store the patient information are closed. It may also occur on an automatic periodic basis, so that the central computer system is updated frequently. It may also occur manually, as a "save" function on the pen computer, to assure that the information is available centrally, and is backed up to the central computer system in case of sudden unforseen problems with the local pen computer.

Figure 4:
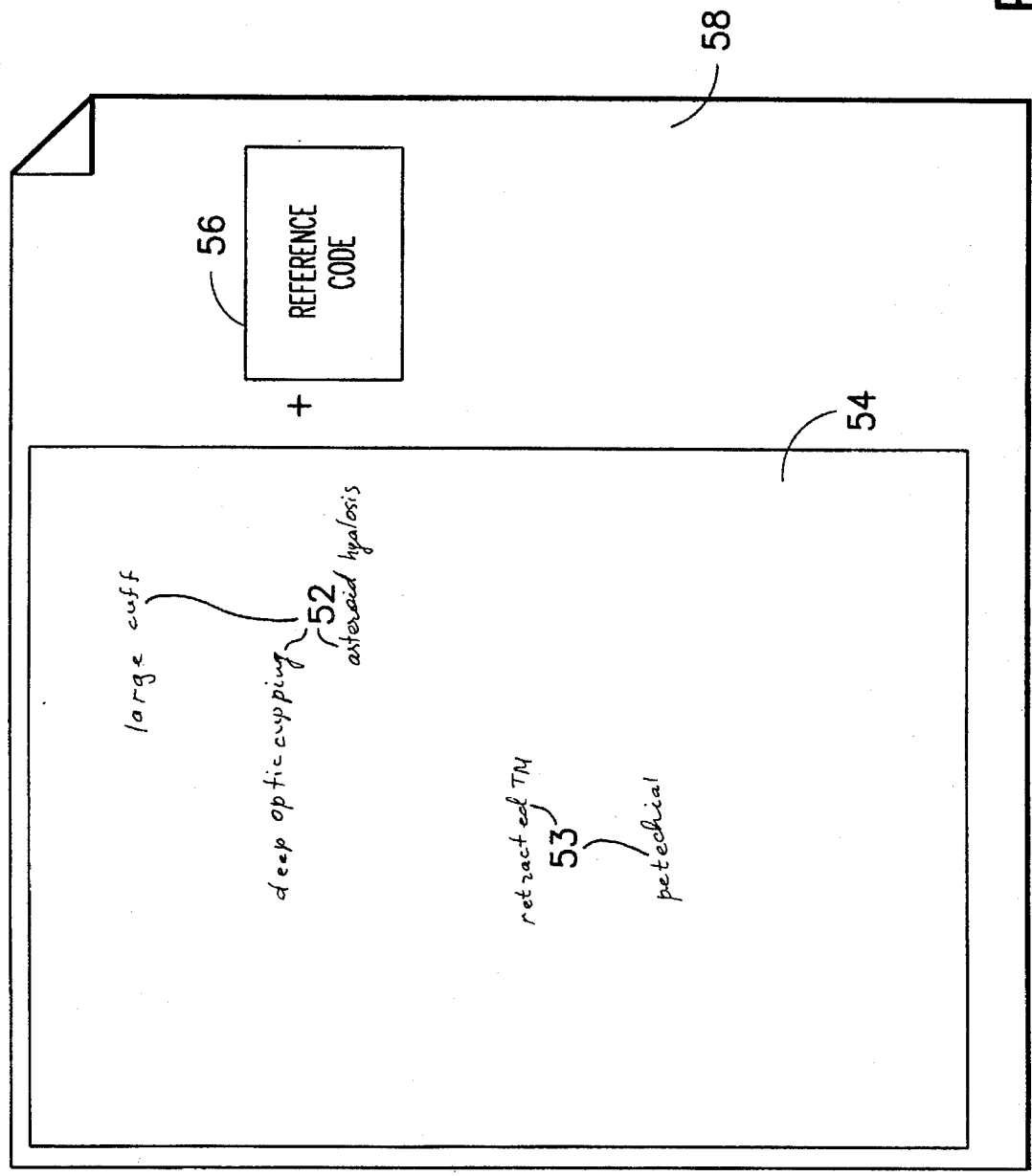
FIG. 4 is a schematic diagram illustrating how electronic ink files are associated with computer generated forms.

Turning now to FIGS. 3 and 3a, certain forms displayed on the display 12a provide spaces within which data may be handwritten. For example, when Physical is selected from the menu 32, the interface 30 displays a page 50 representing the first page of a typical internist's patient physical form. Some fields, 51, contain conventional alphanumeric coded responses, which are entered by selecting items from multiple choice menus, or any other means for selecting or entering text. Preferably, all of the area of the display 12a which is occupied by the page 50 is rendered stylus responsive by the interface 30. In this example, the Physical form is related to a patient John Q. Public, ID#123456789 as seen in headline field 33. According to the methods of the invention, page 50 is carefully mapped so that the relative locations of spaces on the page 50 are always the same. Handwritten notes 52 may be entered anywhere upon page 50 using the stylus 12b (FIGS. 1 and 2) as a pen and the position sensitive display 12a as paper. The interface 30 causes the handwritten notes 52 to appear as they are written on the display 12a. The notes 52 are not interpreted by either the central computer system 10 or the pen-based computer 12. Moreover, no attempt is made to associate any one of the notes 52 with any one part of the page 50. Instead, as shown in FIG. 4, all of the notes 52 are saved as a electronic ink file 54 which represents a graphic image of all of the notes 52 which were written onto page 50 (FIGS. 3 and 3a). The electronic ink file 54 is digitally associated with a reference code 56 to create an identifiable digital document 58. The reference code 56 is selected such that the electronic ink file 54 is associated with a particular form (H&P page 50) and a particular patient (John Q. Public, ID#123456789). The reference code 56 may be digitally associated with the electronic ink file 54 in the form of a file name, in the form of a file header, or a combination of file name and file header. In any case, an identifiable digital document 58 is created. Even though the information (the handwritten notes) contained in the document is unintelligible to the computer, the information can be retrieved and displayed in the context which gives it meaning to a user. For example, once the notes 52 have been written, they can be recalled for display together with the form they are related to on the pen-based computer by selecting the appropriate patient and form page as described above. Now, when page 50 is displayed, digital document 58 will be retrieved and the electronic ink file 54 will be overlaid on top of page 50 as seen in FIG. 3a. Those skilled in the art will appreciate that in order for the notes 52 to be properly displayed on page 50, it is only necessary to remain consistent in the mapping of the page 50 so that the notes align properly with the page. It will further be appreciated that only one digital copy of each form (for example page 50) need be stored in the memory of the central computer system and that the records of a patient will include a plurality of digital documents which include electronic ink and reference to a particular form upon which the electronic ink is to be overlaid.

In addition to handwritten notes 52 placed on any portions of the form, the form may contain data entry fields 51 at fixed positions relative to the form. These data entry fields may contain character coded text, which may be generated by selection from a list, entered on a character-by-character basic via a "virtual" keyboard, or any other convention means of inputting coded characters. Some fields 53 may also contain handwritten information, stored as electronic ink and associated with specific portions of the form rather than associated with the form as a whole. The electronic ink displayed in fields 53 is associated with those fields. By virtue of this association, the electronic ink is given a context specific to particular fields of particular forms. Although it is stored as electronic ink and not interpreted as coded characters, it nonetheless provides important data for specific form fields. For example, the handwriting "retracted TM" in field 53 describes a condition of the tympanic membrane. The positive finding "TM" has been specified by a menu choice under the "ears" fields. The type of tympanic membrane disorder has been written in, and appears in a specific field associated with "ears". Under "pharyngitis", a relatively rare form, "petichial", is written in because it is not common enough to be listed in as a menu choice for pharyngitis. "Petichial" is specifically associated with pharyngitis as a positive finding. When the form is recalled from the central computer system for display on the pen computer, the form fields which contain electronic ink are displayed in their original positions on the form.

Figure 5:
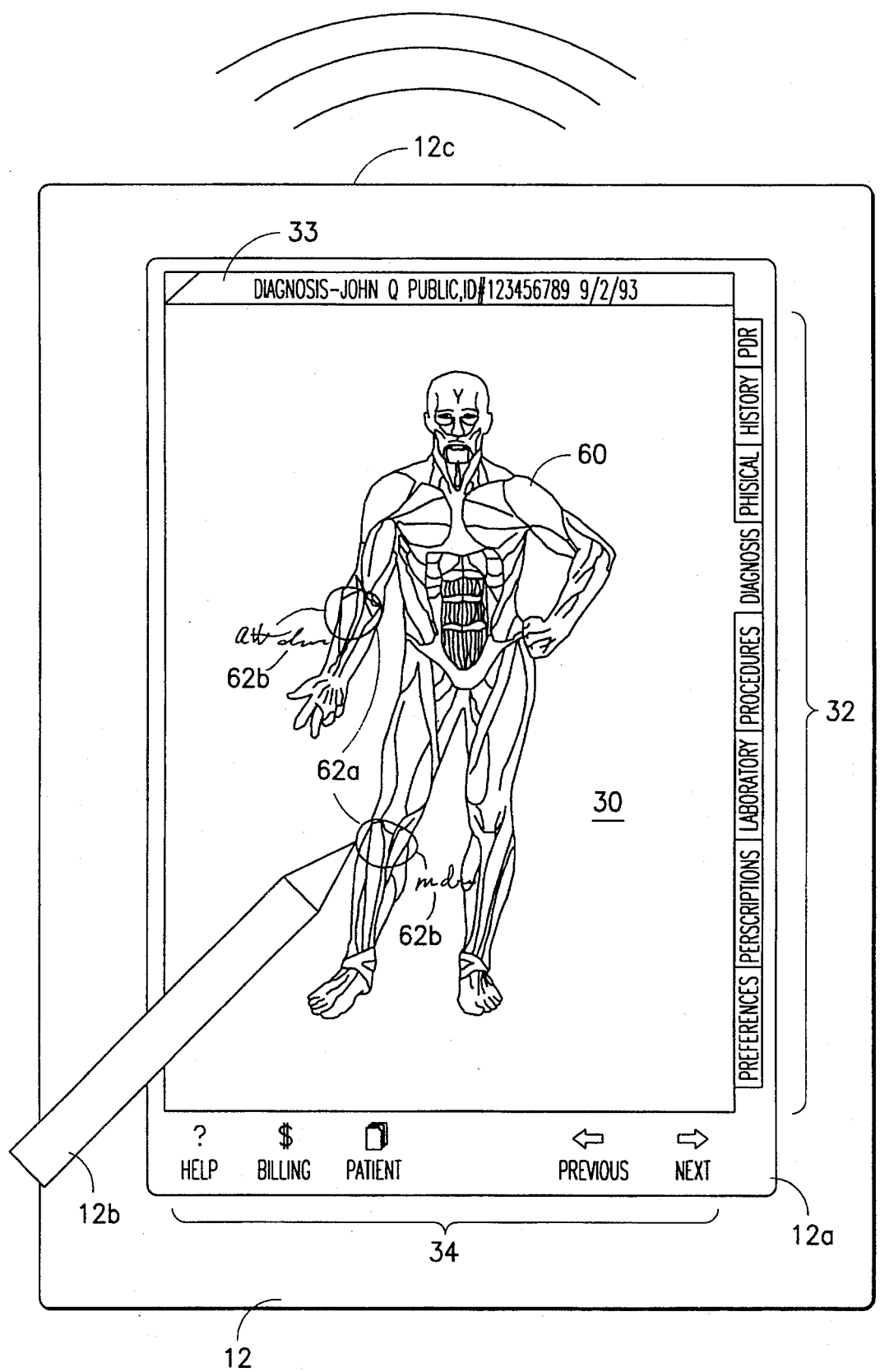
FIG. 5 is a view similar to FIGS. 2 and 3 showing a screen display for entering information in the form of drawings and notes.

In addition to the handwritten notes corresponding to spaces on a standardized form, handwritten drawings may be entered on a template such as the one shown in FIG. 5. FIG. 5 shows how the interface 30 can display a diagram 60 of human skeletal muscles, for example, to aid in patient diagnosis. When such a template is displayed on the position sensitive display 12a, the user can enter drawings 62a and/or notes 62b using the stylus 12b thereby annotating the diagram 60. The annotated diagram 60 becomes a part of the patient records by saving the drawings and notes 62a, 62b as electronic ink as described in more detail below with reference to FIG. 7.

Figure 6:
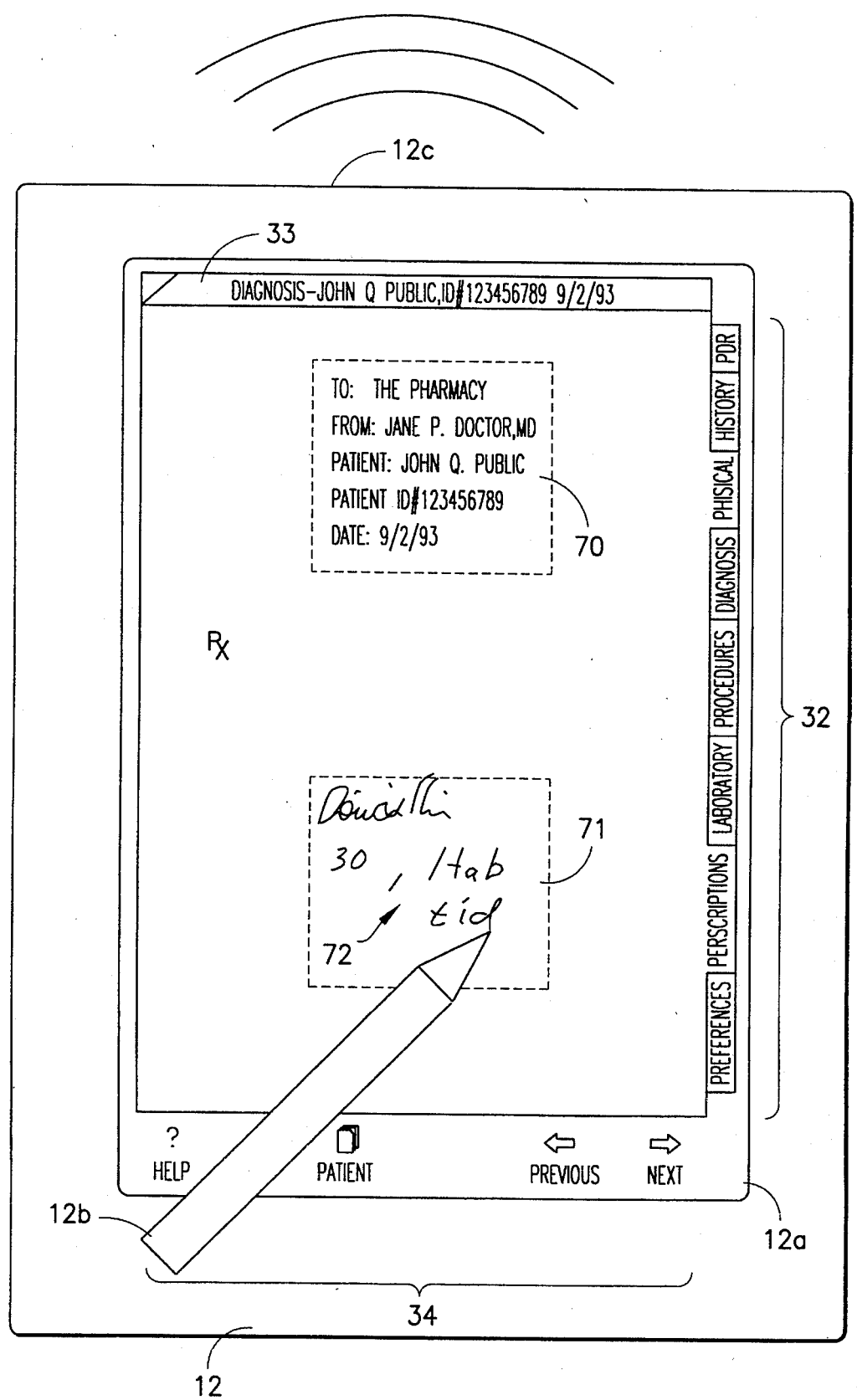
FIG. 6 is a view similar to FIG. 5 showing a screen display for ordering a prescription.

As suggested above, the portable pen-based computer 12 can be provided with powerful communications ability through the wireless network 13. For example, as shown in FIG. 6, when choosing the Prescriptions sub-field from menu field 32, the interface 30 displays prescription fields 70, 71 on the position sensitive display 12a. In this example, a digital header field 70 is automatically displayed with the patient's name, the prescribing doctor's name, the patient ID#, the date, and the name of the Pharmacy chosen to fill the prescription. Those skilled in the art will appreciate that the doctor's name is made known to the computer when the doctor first activates the pen-based computer 12 and is required to enter an access key and/or password. The name of the pharmacy chosen to fill the prescription may default to a pre-selected pharmacy or may be chosen using the stylus 12b and a scrolling multiple choice menu as described above with reference to FIG. 2. Prescription field 71 allows the doctor to enter the prescription in handwriting 72 using the stylus 12b. The handwriting is saved as electronic ink and linked to the prescription form as described in more detail below with reference to FIG. 7. Alternatively, a list of prescription drugs may be displayed and selected in a manner similar to that described above with reference to the diagnosis screen in FIG. 2. A particular drug may be selected using a virtual keyboard and a list of drugs scrolled using the Next and Previous icons. Once a drug has been selected, information about the drug can be displayed using the PDR selection from the menu 32. From the foregoing, it will be appreciated that the interface 30 may define different portions of the display 12a for response to multiple-choice digital input or for the input of electronic ink or for combinations of both. It will further be appreciated that the prescription can be immediately transmitted to the pharmacy through the wireless network 13, or through the modem 11 (FIG. 1) either as a computer file or as a FAX.

Figure 7B:
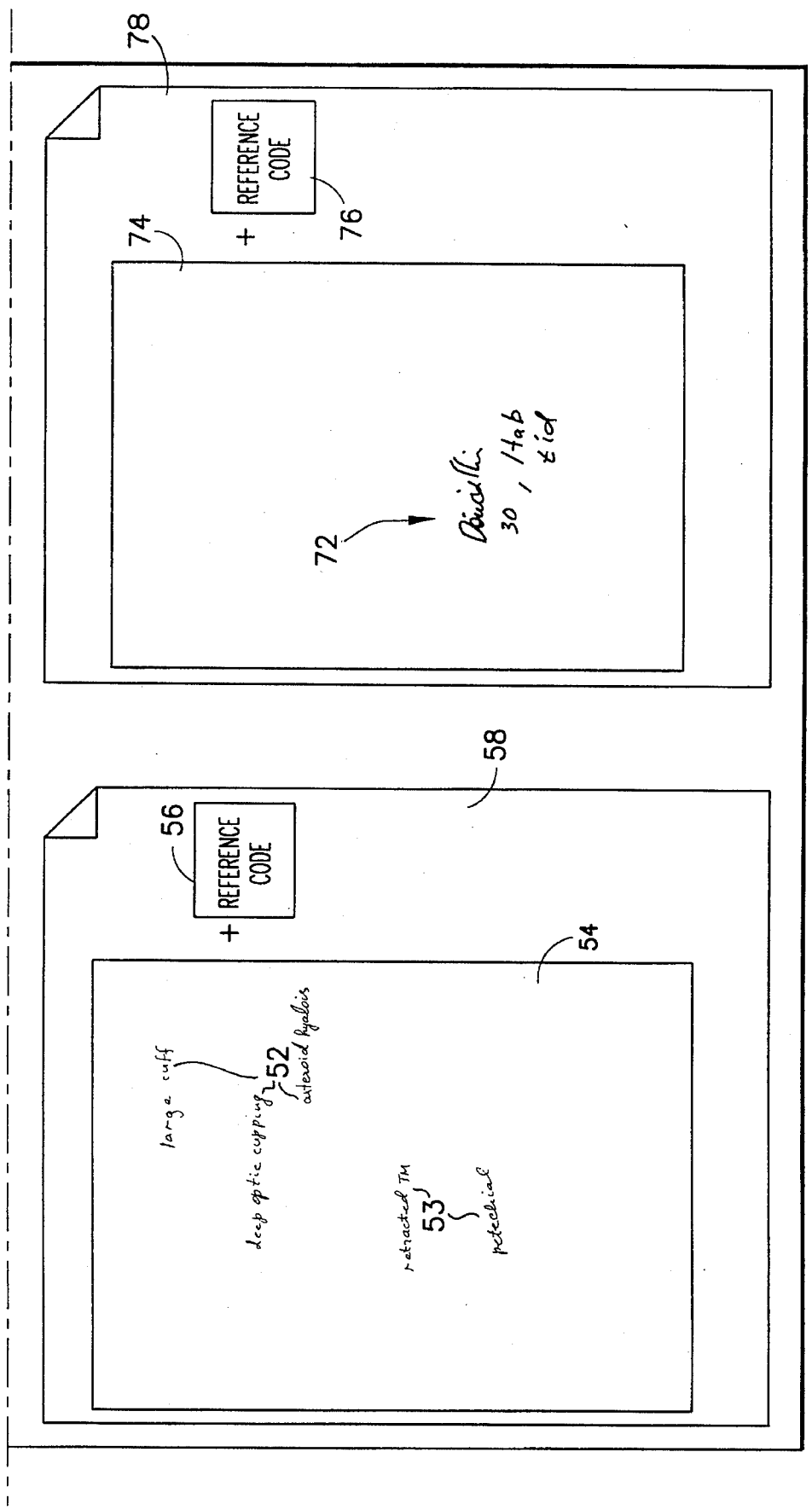
FIG. 7 is a schematic representation of a patient record including a digital data file and electronic ink files.

As mentioned above, all of the information entered in the pen-based computer 12 using the stylus 12b is typically stored in a patient record file. FIG. 7 shows an example of a patient record file 100 which contains a digital data document 41 and identifiable electronic ink documents 58, 68, and 78. Those skilled in the art will appreciate that the digital data document 41 is created from data of the type entered from a multiple choice menu or through a virtual keyboard as described above with reference to FIG. 2. Electronic ink document 58 has been described above with reference to FIG. 4. The electronic ink documents 68 and 78 are those created from the entries described above with reference to FIGS. 5 and 6. The drawing annotations 62a, 62b are saved as a electronic ink file 64 which is coupled with a reference code 66 relating the electronic ink to the particular patient and the particular template or form upon which the electronic ink is to be overlaid thus forming an identifiable electronic ink document 68. Similarly, the prescription information 72 is saved as electronic ink file 74 which is coupled with a reference code 76 relating the electronic ink to the particular patient and the particular template or form upon which the electronic ink is to be overlaid thus forming an identifiable electronic ink document 78. All of the information contained in documents 41, 58, 68, and 78 are grouped together in a single patient record 100 either by concatenation in a single file, by grouping within a single identifiable directory, or by other linking techniques known in the art. These documents are thus linked with a unique patient name and ID# which is shown schematically as 133 in FIG. 7 so that the information may be recalled by any computer having access to the central computer system 10.

Figure 8:
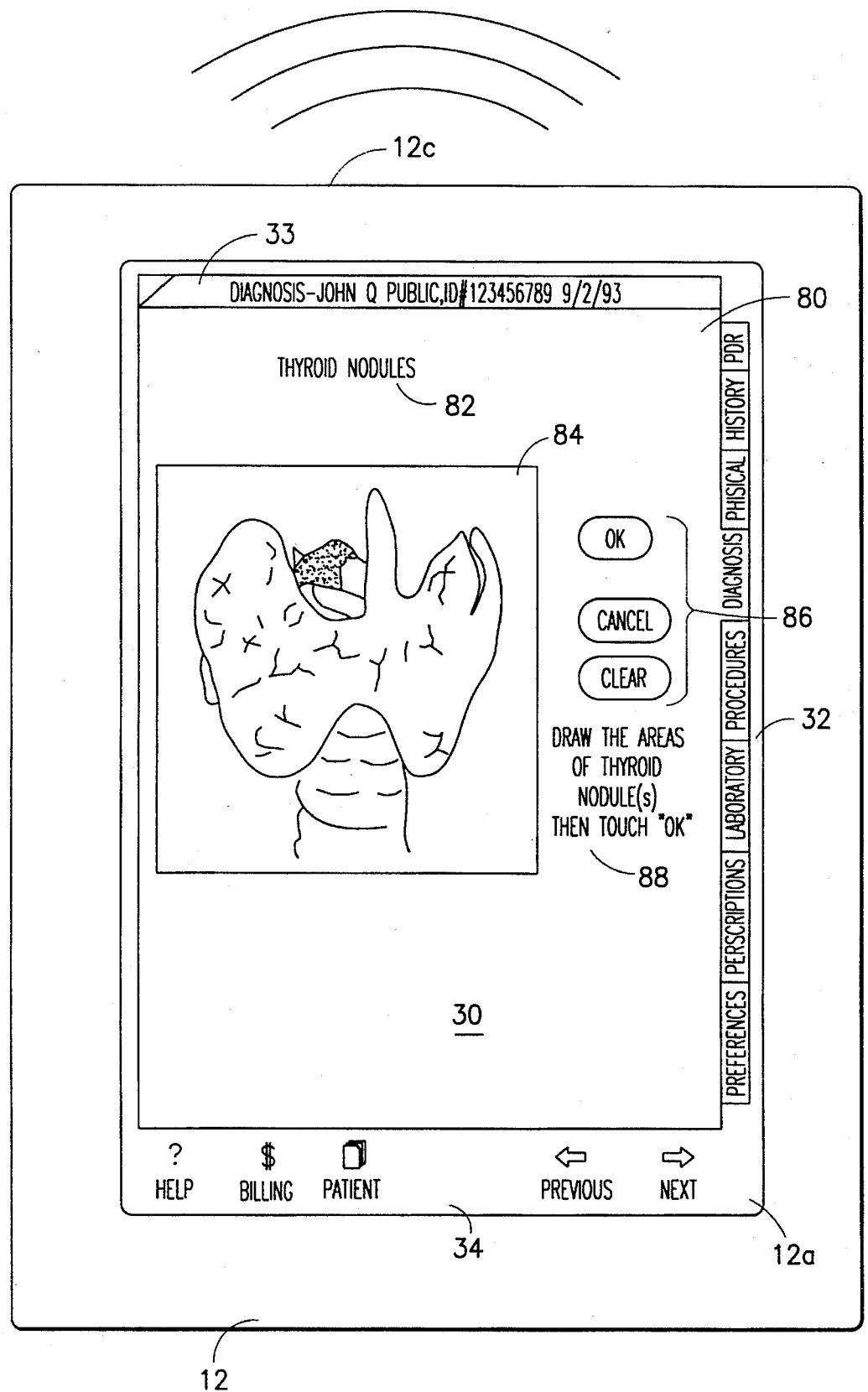

In addition to the annotation of drawings as digital ink described above with reference to FIG. 5, the invention also provides for regions in a drawing to be identified as part of annotating or adding sketches to a drawing. FIG. 8 shows an electronic form 80 designed to accept sketches or annotations for thyroid nodules. The form 80 includes a title field 82 which, in this example indicates "Thyroid Nodules", a graphic illustration 84, control buttons 86, and instructions 88. The form may be drawn upon anywhere in the illustration 84 of the thyroid gland, using the stylus 12b as shown in FIG. 8a with electronic ink marking the drawing. FIG. 8a shows the stylus 12b circling an area 85 on the illustration 84 of the thyroid gland. Upon lifting the stylus 12b from the position sensitive display surface 12a, a region identification algorithm is run for each set of x-y coordinates in the list of display coordinates which constitutes the electronic ink sketch 85. Such region identification algorithms are common in computer graphics, and are used as a means for relating coordinates of a pointing device such as a mouse or stylus to objects displayed on the computer screen. These algorithms are well known to practitioners of the art, and include the QuickDraw™ graphical routine called PtInRgn which is part of the Macintosh™ computer system (Apple Computer, Inc., Cupertino, Calif.), and is used to determine if a given point is contained within an arbitrarily complex shaped region data structure.

Figure 8B:
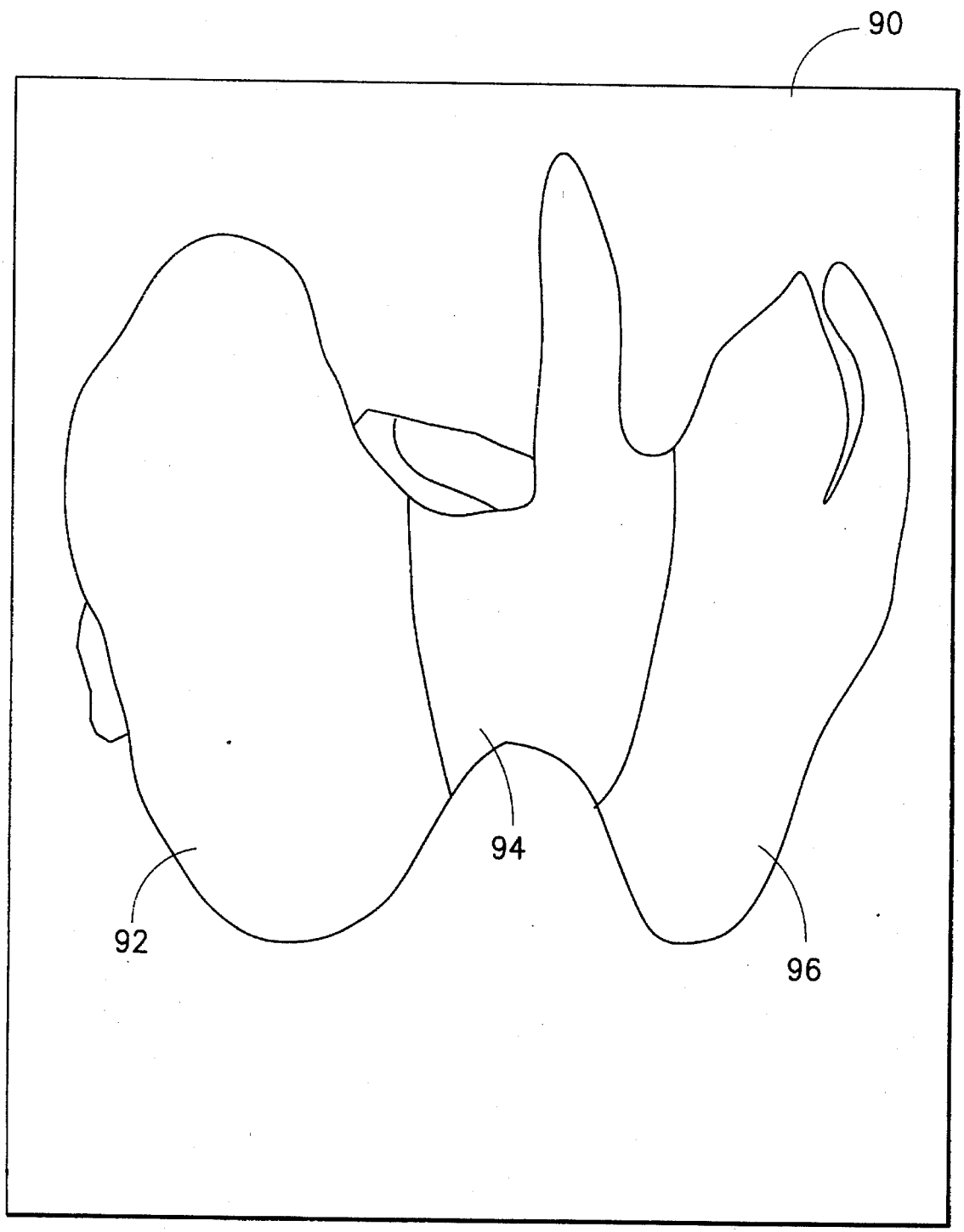
FIG. 8b is a schematic illustration of a regional template used by the graphical interface to determine regions of an illustration indentified by stylus input.
Figure 8B:
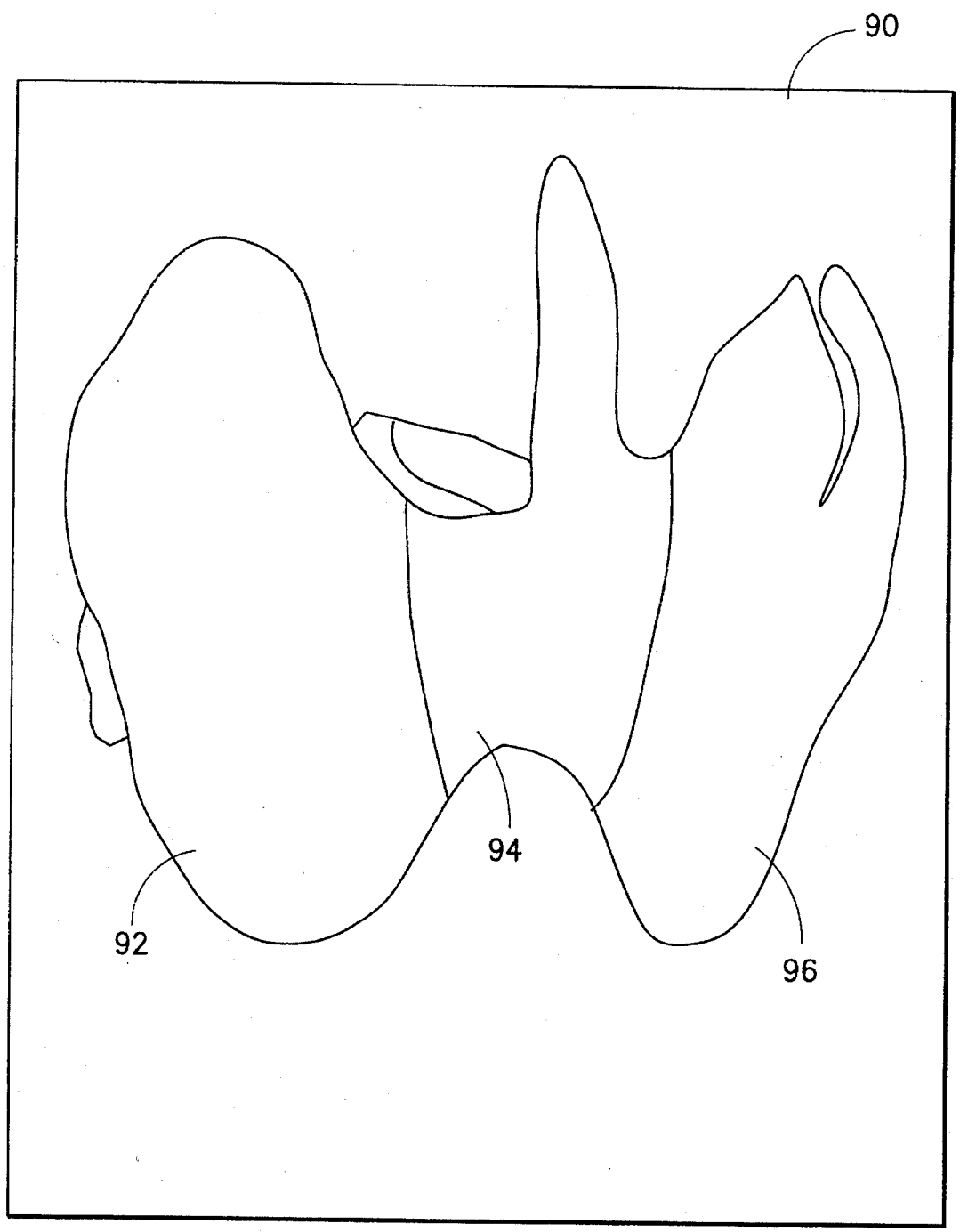

According to the present invention, a region identification algorithm is used not to locate the position of a pointing device, but to determine all relevant regions of an annotation or sketch which electronic ink covers. For example, the circled region 85 in FIG. 8a indicates two relevant regions of the thyroid gland, namely the "right lobe" and the "isthmus". The names of these regions are displayed in field 83. The information selected by touching the stylus to this form, therefore indicates these two regions of the thyroid gland. The two names "right lobe" and the "isthmus" can be stored as coded text. As shown in FIG. 7, this information can be part of a digital document 41 and made part of the patient record 100. FIG. 8b shows a boundary template used by the graphical interface 30 to determine which regions of the thyroid gland are touched by the stylus. For example the contiguous area 92 defines the right lobe, the contiguous area 94 defines the isthmus, and the contiguous area 96 defines the left lobe. When the stylus touches the display in one of these defined areas, the interfaces determines according to the template which region has been indicated. As with the example shown in FIGS. 8 and 8a, using the stylus to draw a circle which touches in areas 92 and 94, identifies the right lobe and the isthmus.

Given all of the above, the method of the present invention, therefore, is to provide a digital template upon which handwritten information can be given a digital meaning without recognizing handwriting as text. The handwritten information is saved as a graphic file having dimensions and resolution which allow it to be overlaid on top of the digital template so that the intended meaning of the handwritten information can be displayed in the context of the digital template upon which it was written. Electronic ink may also be given the context of specific fields within a digital form template, and associated with those specific fields in addition to the overall template. If, at some later date, handwriting recognition technology matures to an acceptable degree of accuracy, the electronic ink graphic files can be subjected to handwriting recognition if desired.

By implementing the method of the invention in a system including portable pen-based computers coupled by a wireless network to a central computer system, the need to collect data with paper and pen is virtually eliminated. There is no need to re-enter data which was first written on paper. There is no loss in the accuracy of the data due to transcription errors, and the data is immediately available through the network to all users who require access to it.

Added advantages of the system of the invention include the ability of the pen-based computers to access a large library of information and to send and receive messages as electronic file transfer or as FAX.

There have been described and illustrated herein a method and system for wireless remote information retrieval and pen-based data entry. While a preferred embodiment of the invention has been described, it is not intended that the invention be limited thereto, as it is intended that the invention be as broad in scope as the art will allow and that the specification be read likewise. Thus, while particular hardware and software has been disclosed in order to implement the invention, it will be appreciated that other hardware and/or software could be utilized to achieve substantially the same results in substantially the same manner. Also, while a specific medical application has been shown, it will be recognized that the invention can be used to advantage in other applications where portable hand written data entry desirable. Moreover, while the interface has been shown as a defined position sensitive display, it will be understood that certain portions of the interface may be replaced by hardware pushbuttons for selecting various menu items, for example. However, according to the invention, at least a portion of the interface must define an area of position sensitive display for the input of electronic ink. It will therefore be appreciated by those skilled in the art that yet other modifications could be made to the provided invention without deviating from its spirit and scope as so claimed.

I claim:

1. A system for wireless remote information retrieval and pen-based data entry, comprising:
    a) a central computer system having memory means containing a plurality of digitally stored forms and for storing data;
    b) a wireless network coupled to said central computer system, said wireless network including at least one transceiver;
    c) at least one portable pen-based computer having a position sensitive display, a stylus for writing on said position sensitive display, and a wireless communication means for communicating with said wireless network through said at least one transceiver;
    d) interface means defining areas on said position sensitive display responsive to said stylus for selecting one of said plurality of digitally stored forms for display on said position sensitive display; wherein
        upon selection of one of said plurality of digitally stored forms, said one of said plurality of digitally stored forms is transmitted by said central computer system to said pen-based computer through said wireless network and is displayed on said position sensitive display,
        handwriting written on said position sensitive display with said stylus is transmitted to said central computer system through said wireless network as electronic ink, and
        said central computer system associates said electronic ink with said one of said plurality of digitally stored forms by creating an association reference code and stores said electronic ink with said association reference code in said memory means for storing data without duplicating said one of said plurality of digitally stored forms so that said electronic ink and said association reference code are stored together with each other, but separate from said one of said plurality of digitally stored forms.

2. A system according to claim 1, wherein:

said central computer system is also provided with read-only memory means containing reference information, and said interface means includes means for selecting said reference information for display on said position sensitive display.

3. A system according to claim 1, wherein:

said wireless network includes a plurality of transceivers, each transceiver defining a communications cell, and said plurality of transceivers are arranged so that adjacent cells overlap.

4. A system according to claim 1, wherein:

said plurality of digitally stored forms include standard medical forms for patient diagnoses, procedures, services, laboratory tests, and prescriptions.

5. A system according to claim 2, wherein:

said plurality of digitally stored forms include standard medical forms for patient diagnoses, procedures, services, laboratory tests, and prescriptions; and said reference information includes the Physician's Desk Reference and the Merck Manual.

6. A system according to claim 1, wherein:

said central computer system is coupled to a modem, and said interface means is provided with means for selecting said electronic ink overlaid with said one of said plurality of digitally stored forms associated with said electronic ink for transmission through said modem.

7. A system according to claim 1, wherein:

said plurality of digitally stored forms includes at least one form listing multiple choice items and when said at least one form is displayed on said position sensitive display, one of said multiple choice items is selected by touching said position sensitive display with said stylus at a location corresponding to said one of said multiple choice items.

8. A system according to claim 1, wherein:

said plurality of digitally stored forms includes at least one form having a graphical illustration and when said at least one form is displayed on said position sensitive display, said graphical illustration is annotated by writing on said position sensitive display with said stylus.

9. A system according to claim 4, wherein:

said interface means includes means for identifying a particular patient and said central computer system associates said electronic ink with said particular patient.

10. A system according to claim 1, wherein:

said plurality of digitally stored forms includes at least one form having a graphical illustration and when said at least one form is displayed on said position sensitive display, a portion of said graphical illustration is identified by touching said position sensitive display with said stylus at a location corresponding to an identifiable portion of said graphical illustration.

11. A method for wireless remote information retrieval and pen-based data entry, comprising:

a) providing a central computer system with a memory means containing a plurality of digitally stored forms and for storing data;

b) coupling said central computer system to a wireless network having at least one transceiver;

c) providing a portable pen-based computer having a position sensitive display, a stylus for writing on said position sensitive display, and a wireless communication means for communicating with said wireless network through said at least one transceiver;

d) displaying an interface on said position sensitive display, said interface including a menu of said plurality of digitally stored forms;

e) selecting one of said plurality of digitally stored forms from said menu;

f) displaying said one of said plurality of digitally stored forms on said position sensitive display;

g) writing handwriting on said position sensitive display with said stylus;

h) transmitting said handwriting as electronic ink to said central computer system;

i) associating said electronic ink with said one of said plurality of digitally stored forms by creating an association reference code; and j) storing said electronic ink with said association reference code in said memory for storing data without duplicating said one of said plurality of digitally stored forms so that said electronic ink and said association reference code are stored together with each other, but separate from said one of said plurality of digitally stored forms.

12. A method according to claim 11, further comprising:

k) providing said central computer system with a library of information stored in read-only memory;

l) providing said interface with a menu of said library of information stored in read-only memory;

m) selecting an item from said menu of said library of information stored in read-only memory;

n) displaying said item of said library of information stored in read-only memory on said position sensitive display.

13. A method according to claim 11, further comprising:

k) providing said interface with means for identifying a particular item of information selected from a list;

l) selecting said item of information from said list using said stylus; and m) associating said item of information selected from said list with said reference code.

14. A method according to claim 11, wherein:

said plurality of digitally stored forms are standard medical forms for patient diagnoses, procedures, services, laboratory tests, and prescriptions.

15. A method according to claim 12, wherein:

said library of information includes medical reference information.

16. A method according to claim 13, wherein:

said item of information identifies a particular human being.

17. A method according to claim 14, wherein:

said reference code includes an identification of a particular human being.

18. A method according to claim 15, wherein:

said medical reference information includes the Physician's Desk Reference and the Merck Manual.

19. A method according to claim 11, further comprising:

k) providing said interface with means for identifying a particular portion of a graphical illustration;

l) selecting said particular portion of said graphical illustration using said stylus; and m) associating said particular portion of said graphical illustration with said reference code.

20. A method according to claim 17, wherein:

said identification of a particular human being is entered through said interface with said stylus from a multiple choice menu.

* * * * *